US012644784B2

(12) United States Patent
Gupta et al.

(10) Patent No.: US 12,644,784 B2
(45) Date of Patent: Jun. 2, 2026

(54) WIRELESS CONTACT FORCE SENSING AND LOCALIZATION

(71) Applicant: THE REGENTS OF THE UNIVERSITY OF CALIFORNIA, Oakland, CA (US)

(72) Inventors: Agrim Gupta, La Jolla, CA (US); Cedric Girerd, La Jolla, CA (US); Manideep Dunna, La Jolla, CA (US); Tania Morimoto, La Jolla, CA (US); Dinesh Bharadia, La Jolla, CA (US); Raghav Subbaraman, La Jolla, CA (US); Qiming Zhang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 419 days.

(21) Appl. No.: 18/554,726

(22) PCT Filed: Apr. 8, 2022

(86) PCT No.: PCT/US2022/023952
§ 371 (c)(1),
(2) Date: Oct. 10, 2023

(87) PCT Pub. No.: WO2022/221129
PCT Pub. Date: Oct. 20, 2022

(65) Prior Publication Data
US 2024/0206996 A1 Jun. 27, 2024

Related U.S. Application Data

(60) Provisional application No. 63/174,226, filed on Apr. 13, 2021.

(51) Int. Cl.
*G01L 1/14* (2006.01)
*G01L 1/10* (2006.01)
(Continued)

(52) U.S. Cl.
CPC ................ *G01L 1/14* (2013.01); *G01L 5/042* (2013.01); *A61B 34/30* (2016.02); *A61B 2090/064* (2016.02); *G01L 1/106* (2013.01)

(58) Field of Classification Search
CPC ... G01L 1/12; G01L 1/18; G01L 5/042; A61B 34/30; A61B 2090/064; A61B 2090/065
See application file for complete search history.

(56) References Cited

U.S. PATENT DOCUMENTS

2013/0192356 A1    8/2013    De Graff et al.
2014/0230563 A1    8/2014    Huang
(Continued)

OTHER PUBLICATIONS

Chu, et al., "Bilinear Feature Fusion Convolutional Neural Network for Distributed Tactile Pressure Recognition and Understanding via Visualization", IEEE Transactions on Industrial Electronics, 2022, vol. 69, No. 6, pp. 6391-6400.
(Continued)

*Primary Examiner* — Jonathan M Dunlap
(74) *Attorney, Agent, or Firm* — Greer, Burns & Crain, Ltd.; Steven P. Fallon

(57) ABSTRACT

A wireless force sensor includes a flexible structure supported opposing a rigid structure with a gap between the flexible structure and the rigid structure. Contact traces on opposing surfaces of the flexible structure and the rigid structure form transmission lines. The contract traces are aligned to contact when a force is applied the flexible structure to cause contact between the traces on the opposing surfaces. Radio-frequency switches modulate a reflected signal from the transmission lines. An antenna receives an interrogation signal transmits the reflected signal.

15 Claims, 9 Drawing Sheets

(51) Int. Cl.
| | |
|---|---|
| *G01L 5/04* | (2006.01) |
| *A61B 34/30* | (2016.01) |
| *A61B 90/00* | (2016.01) |

(56) References Cited

U.S. PATENT DOCUMENTS

| | | |
|---|---|---|
| 2017/0344136 A1 | 11/2017 | Mishalov et al. |
| 2018/0343741 A1 | 11/2018 | Williams et al. |
| 2019/0328245 A1 | 10/2019 | Albu et al. |
| 2021/0075094 A1 | 3/2021 | Da Costa Bras Lima et al. |

OTHER PUBLICATIONS

Huang, et al., "LC Passive Wireless Sensors Toward a Wireless Sensing Platform: Status, Prospects, and Challenges", Journal of Microelectromechanical Systems, 2016, vol. 25, No. 5, pp. 822-841.

Li, et al., "A Miniature Layered SAW Contact Stress Sensor for Operation in Cramped Metallic Slits", Instruments and Experimental Techniques, 2018, vol. 61, No. 4, pp. 610-617.

Li, et al., "IDSense: A Human Object Interaction Detection System Based on Passive UHF RFID", Automation and Interactive Feedback, CHI 2015, pp. 2555-2564.

Li, et al., "Review of Research Status and Development Trends of Wireless Passive LC Resonant Sensors for Harsh Environments", Sensors, 2015, vol. 15, pp. 13097-13109.

Lou, et al., "A Wireless Load Measurement Tool for Spine Surgery", Instrumentation and Measurement, IMTC, 2005, pp. 1813-1817.

Noh, et al., "A Continuum Body Force Sensor Designed for Flexible Surgical Robotics Devices", IEEE, 2014, pp. 3711-3714.

Noh, et al., "A Contact Force Sensor based on S-shaped Beams and Optoelectronic Sensors for Flexible Manipulators for Minimally Invasive Surgery (MIS)", IEEE Sensors Journal, article No. 8854863, pp. 1-9.

Noh, et al., "Multi-Axis Force/Torque Sensor Based on Simply-Supported Beam and Optoelectronics", Sensors, 2016, vol. 16, 1936, pp. 1-22.

Noh, et al., "A Continuum Body Force Sensor Designed for Flexible Surgical Robotics Devices", 36th Annual International Conference of the IEEE Engineering in Medicine and Biology Society, 2014, pp. 3711-3714.

Okamura, et al., "Haptic Feedback in Robot-Assisted Minimally Invasive Surgery", Curr Opin Urol., 2009, vol. 19 (1), pp. 102-107.

Polygerinos, et al., "MRI-Compatible Fiber-Optic Force Sensors for Catheterization Procedures", IEEE Sensors Journal, 2010, vol. 10, No. 10, pp. 1598-1608.

Pradhan, et al., "RIO: A Pervasive RFID-based Touch Gesture Interface", MobiCom, 2017, pp. 261-274.

Ryu, et al., "FBG-based Shape Sensing Tubes for Continuum Robots" IEEE International Conference on Robotics & Automation (ICRA), 2014, pp. 3531-3537.

Shi, et al., "Shape Sensing Techniques for Continuum Robots in Minimally Invasive Surgery: A Survey", IEEE Transactions on Biomedical Engineering, 2017, vol. 64, No. 8, pp. 1665-1678.

Taffoni, et al., "Optical Fiber-Based MR-Compatible Sensors for Medical Applications: An Overview", Sensors, 2013, vol. 13, pp. 14105-14120.

Tan, et al., "A wireless, passive strain sensor based on the harmonic response of magnetically soft materials", Smart Mater. Struct. 17, 2008, pp. 1-6.

Thai, et al., "Design of a Highly Sensitive Wireless Passive RF Strain Transducer", IEEE MTT-S International Microwave Symposium, 2011, pp. 1-4.

Xu, et al., "Curvature, Torsion, and Force Sensing in Continuum Robots Using Helically Wrapped FBG Sensors", IEEE Robotics and Automation Letters, 2016, vol. 1, No. 2, pp. 1052-1059.

Yi, et al., "Passive wireless smart-skin sensor using RFIDbased folded patch antennas", International Journal of Smart and Nano Materials, 2011, vol. 2, No. 1, pp. 22-38.

International Search Report from the corresponding International Patent Application No. PCT/US2022/023952, dated Jun. 2, 2022.

WIRELESS CONTACT FORCE SENSING AND LOCALIZATION

PRIORITY CLAIM AND REFERENCE TO RELATED APPLICATION

The application claims priority under 35 U.S.C. § 119 and all applicable statutes and treaties from prior U.S. provisional application Ser. No. 63/174,226 which was filed Apr. 13, 2021.

STATEMENT OF GOVERNMENT INTEREST

This invention was made with government support under 1935329 awarded by the National Science Foundation. The government has certain rights in the invention.

FIELD

Fields of the invention include force sensing transducers, wireless communications, and robotics.

BACKGROUND

Minimally invasive surgical devices and robots are example tools that can benefit from force sensing. Force sensing allows a robot to detect contact with objects, as well as grasp and manipulate delicate objects if the force sensing is sensitive enough. Despite its many benefits, teleoperated robot-assisted minimally invasive surgery is limited by the inability of current instruments to sense forces applied during surgery. See, A. M. Okamura, "Haptic feedback in robot-assisted minimally invasive surgery," Current opinion in urology, vol. 19, no. 1, p. 102, 2009. Surgeons typically rely upon visual feedback, which only provides indirect evidence of applied forces. Adding force sensing at the tip of a surgical robot or a minimally invasive surgical tool would provide an important tool to reduce the risk of injury. Sensing forces along any portion of the tool or robot that interacts with the patient would also provide valuable information to increase the safety and efficiency of surgical procedures.

Similarly, robot capabilities and human interaction safety would be increase by more sensitive force sensing. The ability of a robot to sensitively sense the force it applies to an object or animal directly affects the scope of possible operations for the robot.

One proposed device for the mechanics of loads transmitted to the spine during scoliosis corrective surgery includes instrumented hooks and screws, and a wireless data acquisition system to measure the loads and moments imposed during scoliosis surgery. E. Lou et al, "A wireless load measurement tool for spine surgery," in 2005 IEEE Instrumentation and Measurement Technology Conference Proceedings, vol. 3, 2005, pp. 1813-1817. This device integrates a standard strain gauge force sensor to regular RF transceivers. Such an arrangement requires power hungry electronic components such as analog to digital converters and RF signal modulators.

Some technologies have been proposed to provide force sensing feedback along the length of minimally invasive surgical tools. Continuum robots are small (diameters as small as 1 millimeter), continuously bending, flexible structures that are especially well-suited for minimally-invasive surgery. Current approaches for sensing forces along the length of these robots include:

Optical fibers. See, P. Polygerinos, et al, "Mri-compatible fiber-optic force sensors for catheterization procedures," IEEE Sensors Journal, vol. 10, no. 10, pp. 1598-1608, 2010; F. Taffoni, et al, "Optical fiber-based mr-compatible sensors for medical applications: An overview," Sensors, vol. 13, no. 10, pp. 14 105-14 120, 2013; C. Shi, X et al, "Shape sensing techniques for continuum robots in minimally invasive surgery: A survey," IEEE Transactions on Biomedical Engineering, vol. 64, no. 8, pp. 1665-1678, August 2017;

Light intensity modulation. See, Y. Noh, et al, "A three-axial body force sensor for flexible manipulators," in 2014 IEEE International Conference on Robotics and Automation (ICRA), 2014, pp. 6388-6393; Y. Noh, et al, "A continuum body force sensor designed for flexible surgical robotics devices," in 2014 36th Annual International Conference of the IEEE Engineering in Medicine and Biology Society. IEEE, 2014, pp. 3711-3714; Y. Noh, et al, "Multi-axis force/torque sensor based on simply-supported beam and optoelectronics," Sensors, vol. 16, no. 11, p. 1936, 2016; Y. Noh, et al, "A contact force sensor based on s-shaped beams and optoelectronic sensors for flexible manipulators for minimally invasive surgery (mis)," IEEE Sensors Journal, vol. 20, no. 7, pp. 3487-3495, 2020.

Published approaches also include Fabry-Perot interferometers and Fiber Bragg Grating (FBG) methods. See, S. C. Ryu and P. E. Dupont, "Fbg-based shape sensing tubes for continuum robots," in 2014 IEEE International Conference on Robotics and Automation (ICRA), 2014, pp. 3531-3537; R. Xu, et al, "Curvature, torsion, and force sensing in continuum robots using helically wrapped fbg sensors," IEEE Robotics and Automation Letters, vol. 1, no. 2, pp. 1052-1059, 2016. These sensors can be costly due to the optical components. The sensors can also suffer from undesired drifts and light intensity loss that can lead to measurement errors.

A recent approach proposes the use of force sensitive resistors to provide feedback in neurosurgery robot tools. See, T. Chen, et al, "Novel, flexible and ultra-thin pressure feedback sensor for miniaturized intra-ventricular neurosurgery robotic tools," IEEE Transactions on Industrial Electronics, pp. 1-1, 2020. A number of these sensors are required to obtain complete measurements of the entire loading state of a robot, and the central lumen of these robots is reserved as passageway for surgical instruments. These constraints therefore lead to a challenge with respect to the placement and wire routing of sensors inside these small structures.

Commercially available sensors that can be made small enough for minimally invasive surgical devices include force sensitive resistors, piezoelectric sensors, capacitive sensors, inductive sensors, optical sensors, ultrasonic sensors, magnetic sensors, electromagnetic (EM) tracking systems, and electrical impedance tomography sensors. While the sensors themselves can be small, the sensors require either wires or additional electronics to communicate data. Additional electronics are required for wireless communication, as sensor outputs require encoding for wireless communication. Additionally, these sensors require a power or light source, which makes them unsuitable for very small robotic instruments or in constrained environments.

Some wireless force sensors have been proposed. One type uses LC resonant circuits. C. Li, et al, "Review of research status and development trends of wireless passive lc resonant sensors for harsh environments," Sensors, vol. 15, no. 6, pp. 13 097-13 109, 2015 However, these require a close interrogation distance between the sensor and the readout circuits—on the order of magnitude of a centimeter. The LC resonant sensors are also easily affected due to misalignment, noise from the environment, and cross-talking among elements. Q.-A. Huang, et al, "Lc passive wireless sensors toward a wireless sensing platform: status, prospects, and challenges," Journal of Microelectromechanical Systems, vol. 25, no. 5, pp. 822-841, 2016.

Another type of wireless sensor uses electromagnetically soft materials. E. L. Tan, et al, "A wireless, passive strain sensor based on the harmonic response of magnetically soft materials," Smart Materials and Structures, vol. 17, no. 2, p. 025015, 2008. These require multiple large coils in close proximity to the sensor, which is not practical for most applications in confined spaces.

Wave backscattering has been used to sense binary contact information, i.e., contact or a lack of contact. See, e.g., S. Pradhan, et al, "Rio: A pervasive rfid-based touch gesture interface," in Proceedings of the 23rd Annual International Conference on Mobile Computing and Networking, 2017, pp. 261-274; H. Li, et al, "Idsense: A human object interaction detection system based on passive uhf rfid," in Proceedings of the 33rd Annual ACM Conference on Human Factors in Computing Systems, 2015, pp. 2555-2564. Binary information is insufficient for many force sensing applications, including for sensitive minimally invasive surgical tools.

A SAW (Surface Acoustic Waves) based strain sensor relies on backscattering and has been proposed to sense analog forces. H. Li, et al, "A miniature layered saw contact stress sensor for operation in cramped metallic slits," Instruments and Experimental Techniques, vol. 61, no. 4, pp. 610-617, 2018; X. Yi, et al, "Passive wireless smart-skin sensor using rfid-based folded patch antennas," International Journal of Smart and Nano Materials, vol. 2, no. 1, pp. 22-38, 2011; T. T. Thai, et al, "Design of a highly sensitive wireless passive rf strain transducer," in 2011 IEEE MTT-S International Microwave Symposium. IEEE, 2011, pp. 1-4; J. Humphries and D. Malocha, "Passive, wireless saw ofc strain sensor," in 2012 IEEE International Frequency Control Symposium Proceedings. IEEE, 2012, pp. 1-6. These sensors use a small slit. The devices sense the elongation caused by strain along the length of the sensor, by sensing the antenna's resonant frequency. Basically, these devices use the antenna as the sensor, since due to applied strain the antenna elongates which changes its resonant frequency. The resonant frequency is then measured by estimating the amplitude variation across frequencies. Sensitivity to small forces is limited by the sensing method and antenna distortion can lead to multipath interference.

SUMMARY OF THE INVENTION

A preferred embodiment provides a wireless force sensor. The sensor includes a flexible structure supported opposing a rigid structure with a gap between the flexible structure and the rigid structure. Contact traces on opposing surfaces of the flexible structure and the rigid structure form transmission lines. The contract traces are aligned to contact when a force is applied the flexible structure to cause contact between the traces on the opposing surfaces. Radio-frequency switches modulate a reflected signal from the transmission lines. An antenna receives an interrogation signal transmits the reflected signal.

DETAILED DESCRIPTION OF THE PREFERRED EMBODIMENTS

Figure 1:
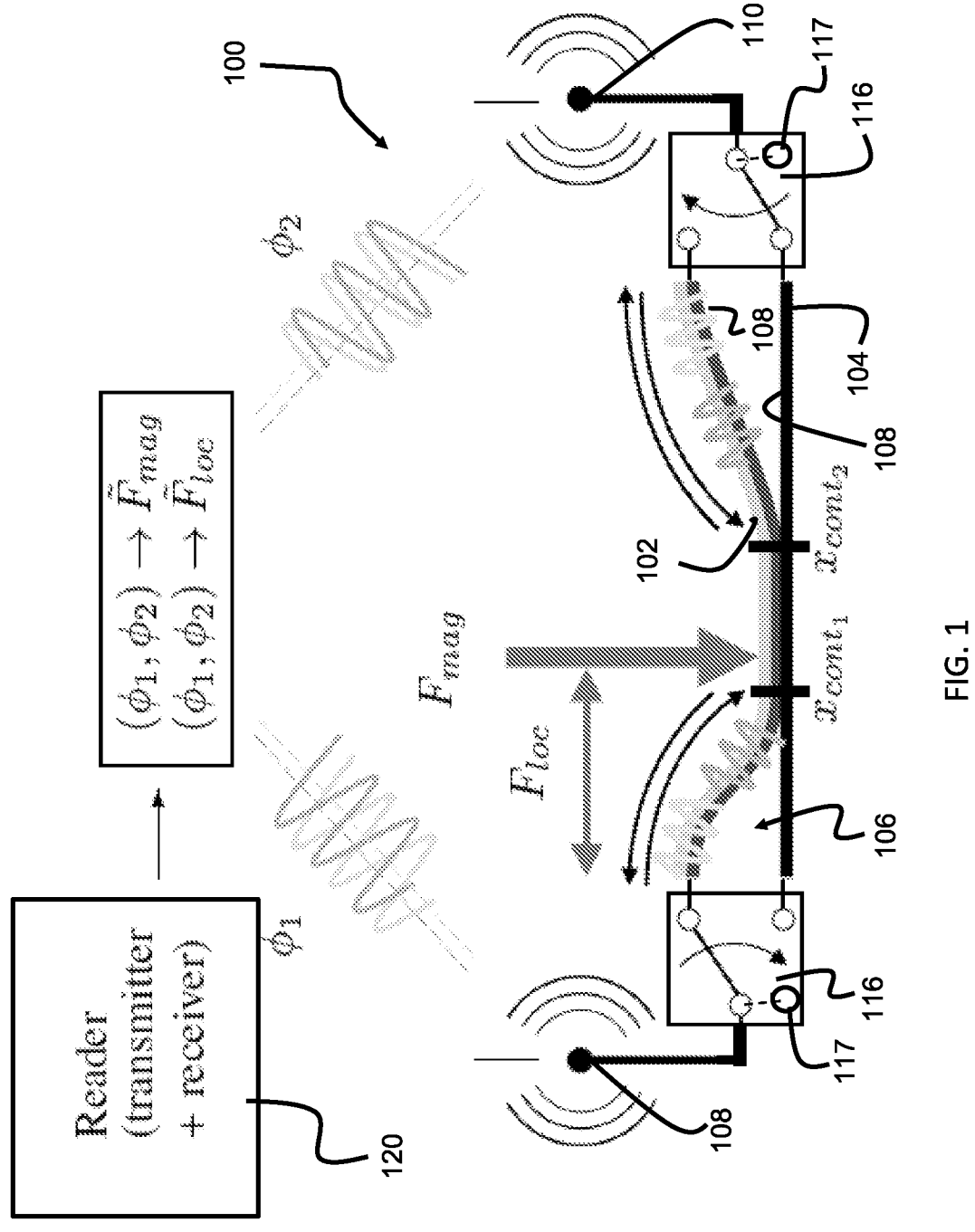
FIG. 1 is a schematic diagram of a preferred embodiment force sensor system of the invention.

A preferred embodiment provides a force sensor that transduces contact force information into wireless signal phase changes, which can be read by a wireless reader. The reader first transmits a wideband RF signal, which the sensor backscatters with phase changes, and the reader receives back the phase changed signal. The phase change is then read at multiple frequencies using the wideband capabilities of the reader for a very robust phase change detection that can be translated into force magnitude and location, while the sensor can meet ultra-low power requirements. A preferred sensor can be attached to an object or robot, like a sticker. A preferred sensor can be powered via an RF energy harvester, and thus allows the sensor to be "batteryless". The lack of need for a local battery source is a key advantage in many applications, including force sensing applications to surgical robots An example sensor of the invention is supports wide-band frequencies, e.g. up to 3 GHz. Experiments demonstrated force sensing wirelessly in different environments, including in-body like, and demonstrated force accuracy of 0.3 N and contact location accuracy of 0.6 mm.

A preferred sensor includes or consists of a beam with a microstrip line (forming a force continuum surface), 2 RF switches, and one antenna to communicate the backscattered phases to the wireless reader. A sensor can also include a clock source, a splitter to combine outputs of the 2 RF switches. The clock, splitter and power, e.g. battery or energy harvester, can be conventional low-power microcomponents. The microstrip line consists of two parallel conducting traces, the signal trace, and the ground trace. A force applied to the microstrip line causes the traces to bend and come in contact, which shorts the line and leads to signal reflections. The reflections produced by the shorting have different phase properties based on the location of the short(s). The force continuum surface directly embeds the force magnitude and location information in properties of a signal reflected from the antenna. Such reflection requires minimal power, which can be harvested and therefore simplifies the sensor design.

A preferred sensor includes a contact force beam suspended over a shorting surface. The beam includes a signal trace over microstrip RF lines to make the lines force sensitive. The degree of bending of the top beam, when contacted centrally creates more shorting points that move toward the end beams in a symmetrical pattern. The location of bending also creates a different asymmetrical pattern of shorting points. The pattern of shorting points provides transduction of force magnitude and location via a change in the phase of the reflected signal from both ends. This allows the sensor to transduce the force magnitude and location onto the reflected signal phases, to facilitate extremely low-powered force sensing, to be transmitted via an antenna, or in another variation via more than one antenna, e.g., an antenna at each end. The sensor includes RF-switches, which are toggled to provide electrical isolation to combat intermodulations, and at the same time also provides different identities to these ends in terms of different frequency shifts.

An experimental sensor was fabricated with ecoflex soft-polymer material with bending properties that maximize the phase changes transduced by contact forces. That sensor included RF-switches and an antenna. The power consumption of our sensor including the switch toggling and clock is under 1 μW evaluated in TSMC technology node of 65 nm, as flip chip package. The fabricated sensor works for the entire sub-3 GHz verified with the test equipment (vector network analyzer).

A preferred reader includes a sensing method that utilizes wideband channel estimates to isolate the signal from multipath in Doppler domain. Finally, by grouping the channel estimates into 'phasegroups', the reader can read phase changes over multiple subcarriers which allows for averaging gains to make the phase sensing robust and accurate.

Preferred embodiments of the invention will now be discussed with respect to experiments and drawings. Broader aspects of the invention will be understood by artisans in view of the general knowledge in the art and the description of the experiments that follows.

FIG. 1 shows a preferred embodiment sensor 100. The sensor includes a multilayer, e.g., bilayer, beam 102 supported in way that it is normally (under a condition of no or insignificantly applied force) separated from a rigid base 104 by an open gap 106. The beam 102 can be deflected and depending upon the amount of force will make contact at different locations with the base 104. The edges of the contact length between the beam 102 and base 104 are denoted $xcont_1$ and $xcont_2$. The beam 102 and base 104 include contact traces 108 opposing each other such that electrical contact is made when the beam 102 contacts the base 104. The contact traces are transmission lines that carry electromagnetic waves through two antennas 110 located at both ends of the base 104. RF switches 116 modulate a reflected signal that have shifted phases compared to an interrogation signal. The RF switches 116 including a clock can be selected to have power requirements of a few uW, which can be fulfilled with a small energy harvester or battery 117. In an example prototype, 3.3 uW was consumed for switching and clocking. Overall, the design can readily meet <10 uW, which works well with energy harvesters. The shifted phases, denoted Ø1 and Ø2 after reflection, are measured by a reader 120 and used to determine the applied force magnitude ($F_{mag}$) and location ($F_{loc}$). While the contact traces 108 can be straight transmission lines, meander or other geometry lines can also be used. Meander lines can meet frequency requirements while allowing a more compact size for the sensor. Similarly, while the beam 102 and the base 104 are shown as being straight and parallel, these components can be complementary half or full tubular shapes with a gap between.

The bilayer beam 102 is configured to deform uniquely upon application of a given force magnitude and application location, such that different force magnitudes and locations provide additional unique deformations of the beam and contact patterns with the base 104. The top layer of the bilayer beam 102 is stiffer than its bottom layer, such that the applied force is distributed onto the softer bottom layer, leading to an increasing contact length with the rigid base as the applied force is increased. The softer layer can be a polymer, e.g., silicone, PDMS. Soft silicone rubbers are preferred. The stiffer layer can be an acrylic or other plastic. Thermoplastic materials are preferred. The location of the contact edges between the bilayer beam and the rigid base informs the reader 120 of the force magnitude and location that is applied to the beam 102. More than two layers can be used in the beam 102, and/or the properties of the layers can be varied along the beam length, for example to create more complex stiffness profiles over the length of the beam, e.g., stiffer in the middle and softer near the supports. The beam 102 could also be tailored such that a particular portion is more sensitive to an external force by having an overall softer profile at that portion.

The trace 108 on the bilayer beam is a signal trace, while the trace 108 on the base 104 is the ground trace. The signal trace converts the mechanical contact locations $xcont_1$ and $xcont_2$ between the bilayer beam 102 and the rigid base 104 into electrical shorting locations. This causes a reflection of emitted electromagnetic waves at the shorting locations when the sensor 102 is interrogated by the reader 120 with electromagnetic energy. The reader 120 senses the phases Ø1 and Ø2 after reflection. The RF switches 116 modulate the reflected signal before it is re-emitted, which helps the reader 120 distinguish an interrogation signal from a reflected sensor signal. Switching sequences help isolate the reflections from the sensor amongst the myriad of reflected signals received by the reader 120.

Beam 102 Design Considerations.

The equivalent bending stiffness D of a beam composed of n layers is given by Eq. (1), where $E_i$ is the Young's modulus of the i-th layer, and $I_i$ is its moment of inertia:

$$D = \sum_{i=1}^{n} E_i I_i \qquad (1)$$

Figure 2:
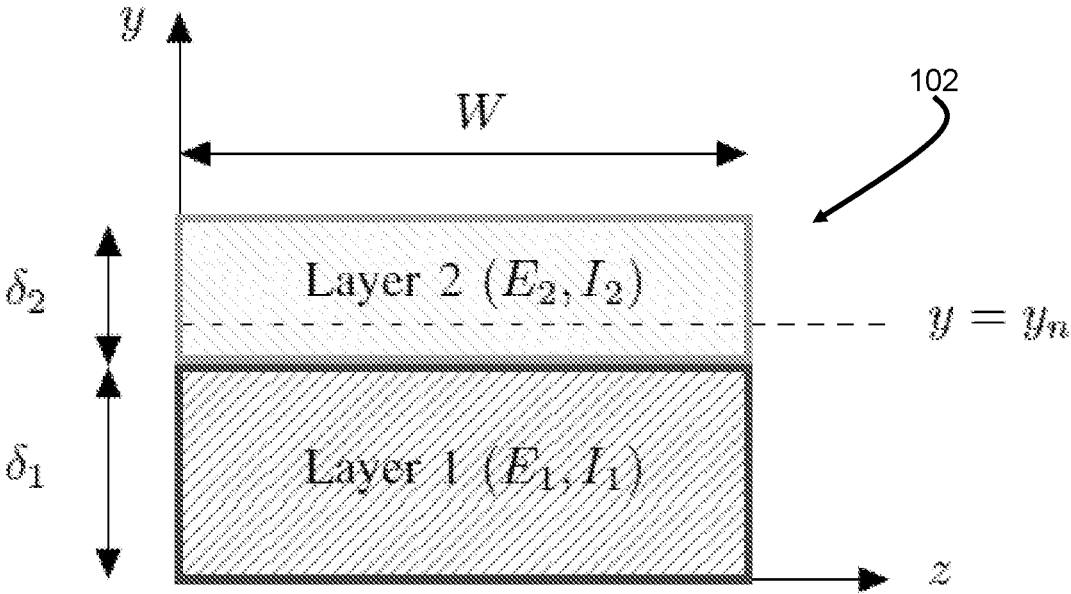
FIG. 2 is a schematic side view of preferred bilayer beam for the sensor in the sensor system of FIG. 1.

While the Young's modulus of the i-th layer only depends on the material of that particular layer, $I_i$ depends on the location of the neutral fiber of the multilayer beam assembly, $y_n$, as visible in FIG. 2 in the case of 2 layers for the beam 102. The position of the neutral fiber is given by Eq. (2):

$$y_n = \frac{\sum_{i=1}^{n} B_i \delta_i + 2\sum_{i=2}^{n}\left(B_i \sum_{j=1}^{i-1}\delta_j\right)}{2\sum_{i=1}^{n} B_i} \qquad (2)$$

Where $\delta_i$ is the thickness of the i-th layer of the multilayer beam, and $B_i = E_i A_i$, with $A_i = \delta_i w$. The moment of inertia, $I_i$, of each layer is then computed using Eq. (3):

$$I_i = \frac{W\delta_i^3}{12} + W\delta_i y^{*2} \qquad (3)$$

with $$y^* = y_n - 0.5\delta_i - \sum_{m=1}^{i-1}\delta_m \qquad (4)$$

In the case of a beam composed of two layers (i.e. a bilayer beam), as is the case for our application, the bending stiffness, D, given by Eq. 1, reduces to Eq. 5:

$$D = W\left(\frac{E_1^2\delta_1^4 + 4E_1E_2\delta_1^3\delta_2 + 6E_1E_2\delta_1^2\delta_2^2 + 4E_1E_2\delta_1\delta_2^3 + E_2^2\delta_2^4}{I_2(E_1\delta_1 + E_2\delta_2)}\right) \quad (5)$$

To use the equations from beam mechanics, we assume that the beam satisfies Euler-Bernoulli's hypothesis. The hypothesis is satisfied if Eq. (6) holds, where E is the Young's modulus of the beam, I its cross-sectional moment of inertia, $\kappa$ the Timoshenko shear coefficient, L the beam length, A its cross-sectional area, and G its shear modulus. In the case of a beam with a rectangular cross-section, $\kappa=\frac{5}{6}$. For a bilayer beam, we assess the validity of Eq. (6) in the extreme case where the beam is comprised of two layers made (i) solely of material 1 and (ii) solely of material 2, which is sufficient to validate the hypothesis and covers all thickness ratios between these two extremes.

$$\frac{EI}{\kappa L^2 AG} \ll 1 \quad (6)$$

The deflection y(x) of the bilayer beam subject to a point force is obtained by expressing the moment balance $M_z(x)$ along the bilayer beam in the regions $x \in [0, F_{loc}]$ and $x \in [F_{loc}, L]$ and calculating $$\frac{\delta^2 y(x)}{dx^2} = \frac{M_z(x)}{D},$$

and leads to the expressions in Eq. (7):

$$y(x) = \begin{cases} \dfrac{F_{mag}x^2(L - F_{loc})^2(Lx - 3LF_{loc} + 2F_{loc}x)}{6DL^3} \\ \qquad \text{if } x \in [0, F_{loc}] \\ \dfrac{F_{mag}F_{loc}^2(L - x)^2(LF_{loc} - 3Lx + 2F_{loc}x)}{6DL^3} \\ \qquad \text{if } x \in [F_{loc}, L] \end{cases} \quad (7)$$

with D being the bending stiffness of the bilayer beam, given by Eq. (1). The maximum deflection $y_{max}$ of the bilayer beam, and the location of this maximum deflection along it, are then obtained by solving $$\frac{dy(x)}{dx} = 0,$$

leading to Eq. (8):

$$y_{max} = \begin{cases} \dfrac{2F_{mag}F_{loc}^2(L - F_{loc})^3}{3D(3L - 2F_{loc})^2} \quad \text{at } x = \dfrac{L^2}{3L - 2F_{loc}} \\ \qquad \text{if } F_{loc} \leq L/2 \\ \dfrac{2F_{mag}F_{loc}^3(L - F_{loc})^2}{3D(L + 2F_{loc})^2} \quad \text{at } x = \dfrac{2LF_{loc}}{L + 2F_{loc}} \\ \qquad \text{if } F_{loc} \geq L/2 \end{cases} \quad (8)$$

The two solutions in Eq. (8) are demonstrated symmetric about $$x = \frac{L}{2},$$

by using the change of variable $F_{loc} \rightarrow L - F_{loc}$. For this reason, only one half of the sensor needs to be studied. We consider forces applied to the first half $$\left(F_{loc} \leq \frac{L}{2}\right).$$

Figures 3A, 3B:
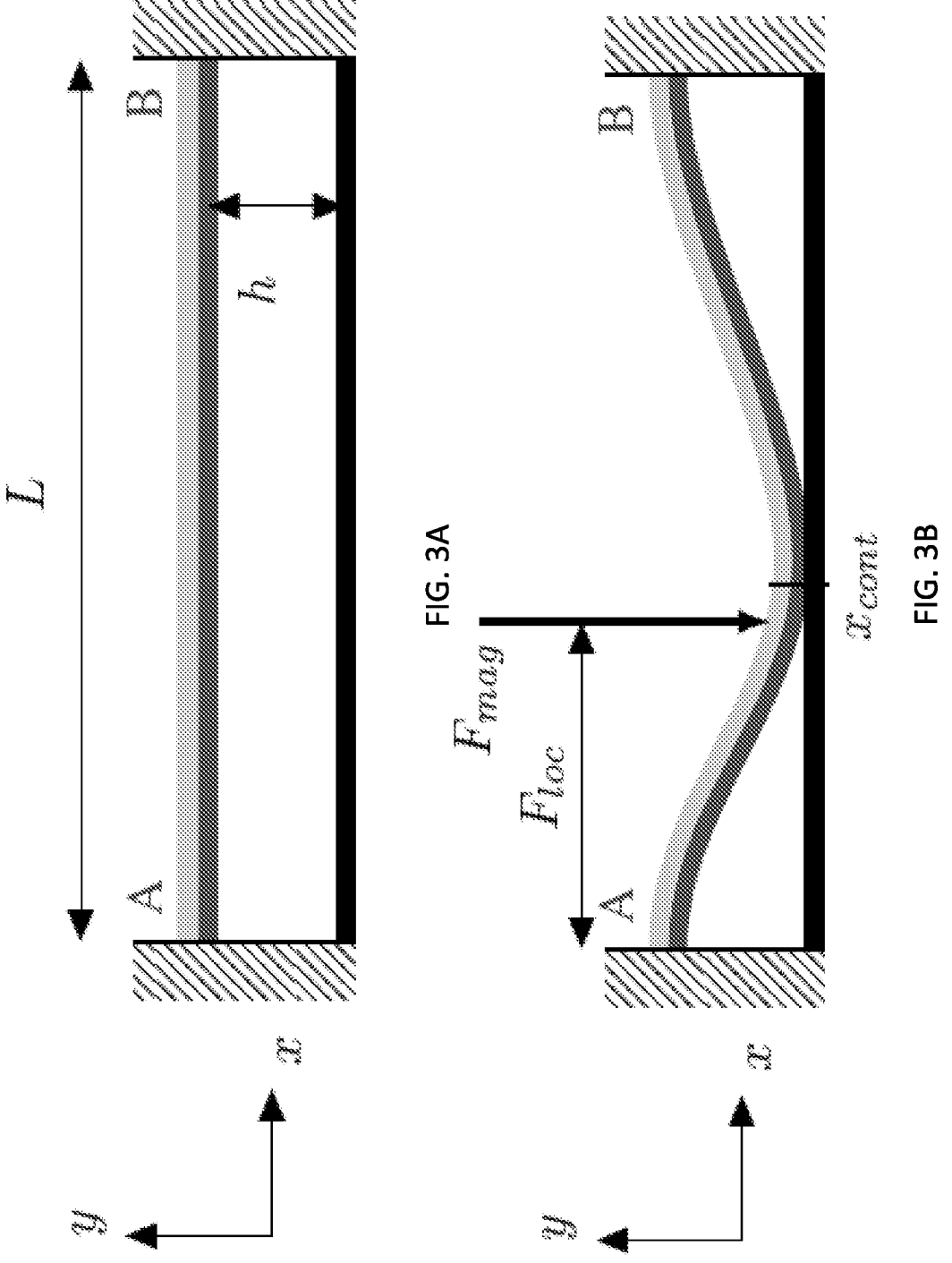
FIGS. 3A and 3B illustrate respective rest and initial contact between the bilayer beam and rigid base for the invention.

The initial contact between the bilayer beam and the rigid base is obtained for a maximum deflection of the bilayer beam $y_{max} = h$ (represented in FIGS. 3A and 3B), which leads to Eq. (9) that must hold for $$F_{loc} \leq \frac{L}{2}.$$

$$h = \frac{2F_{mag}F_{loc}^2(L - F_{loc})^3}{3D(3L - 2F_{loc})^2} \quad (9)$$

The contact location between the bilayer beam and the rigid base is at $x = x_{cont}$, with $x_{cont}$ given by Eq. (10) (see FIG. 3B).

$$x_{cont} = \frac{L^2}{3L - 2F_{loc}} \quad (10)$$

As visible in Eq. (10), there is unicity between the contact location between the bilayer beam and the rigid base, $x_{cont}$, and the location of application of the force on it, $F_{loc}$, which allows a unique mapping between them. Then, we observe that for a particular sensor, as $F_{loc}$ decreases to 0, $F_{mag}$ must tend to infinity for Eq. (9) to hold, which means that the proposed mechanical transducer has edge effects. To ensure that forces of a given magnitude can be sensed, Eq. (9) must be verified for the smallest values of $F_{loc}$. In addition, Eq. (9) allows us to define a relationship between the minimum force that can be sensed by the sensor and all of its mechanical design parameters, which is suitable for design optimization purposes. Indeed, the bilayer beam deflection for initial contact, h, is an increasing function of L and a decreasing function of D, and therefore a decreasing function of W, $E_1$, $E_2$, $\delta_1$, $\delta_2$. By adjusting these design variables, desired performance can be obtained in terms of the minimum force that can be detected along the sensor length.

Figure 4:
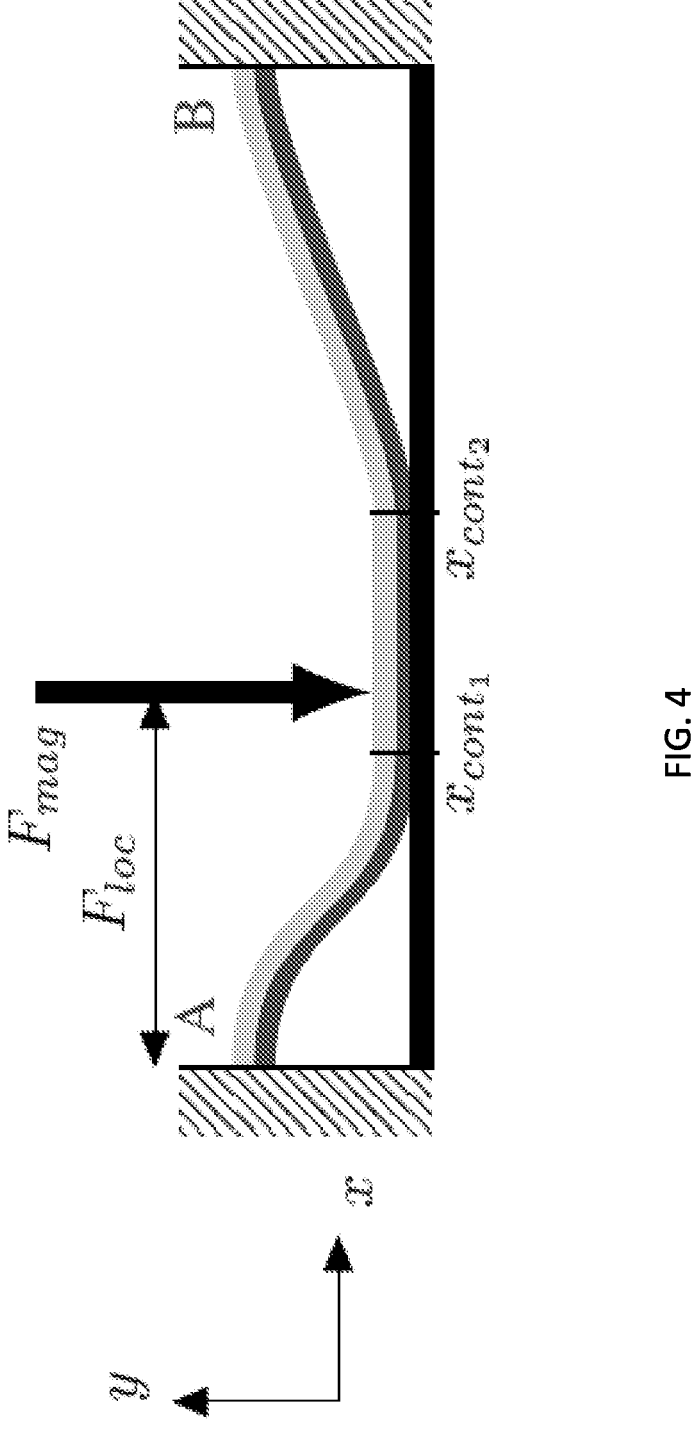
FIG. 4 illustrates an example sensor responding to an applied force and the resulting contact locations between the bilayer beam and base.
Figure 5:
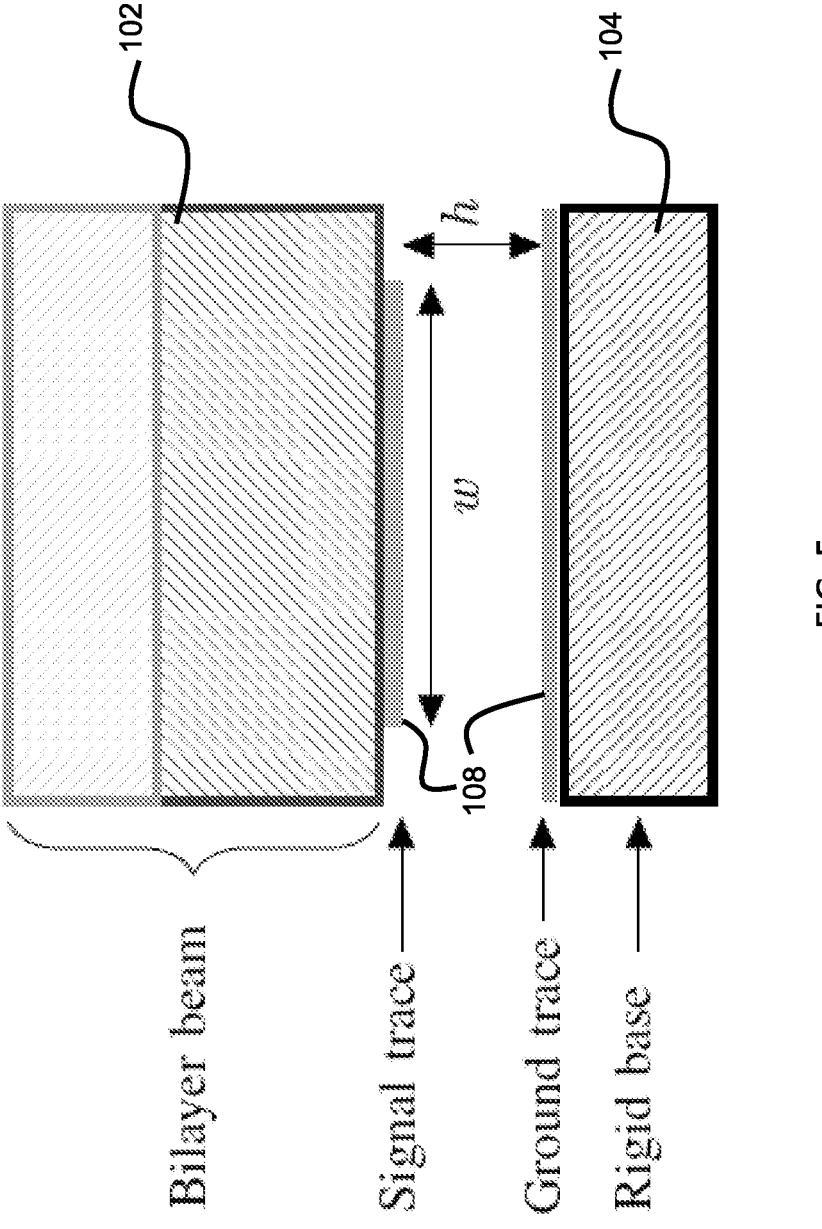
FIG. 5 is a schematic side view of preferred bilayer beam, contact traces and base for the sensor in the sensor system of FIG. 1.

After initial contact, as both beams are pressed against each other, beam mechanics is no longer applicable, and finite element analysis is thus used to model the contact between them. FEA is used to compute the location of the contact edges $x_{cont1}$ and $x_{cont2}$ between the bilayer beam and the rigid base, as illustrated in FIG. 4. An increase in applied force corresponds to an increase in contact length between the beams around the initial contact point predicted by the bilayer beam mechanics model. A critical requirement for the sensor is that the displacement of these contact edges should lead to significant phase changes that are measurable and provide sufficient force magnitude and application location resolution. The contact edge location requirements are set by the trace design and wireless phase measurement approach. They should be selected to lead to the selection of the design parameters L, w, $E_1$, $E_2$, $\delta_1$, $\delta_2$ and h of the sensor that, while respecting Eq. (8), will allow a design to have the desired contact edges between the bilayer beam and the rigid base.

Electrical Trace Design

For the sensor to be compatible with connected electrical components, i.e. antennas, it must match the impedance of such components. A common, widely adopted standard is an impedance of 50Ω, so the sensor is preferably designed to match this value. The sensor can be seen as analogous to two parallel microstrips, separated by a dielectric—in this case, air. With such a representation, the impedance of the sensor has a known expression given by Eq. (11) in the case of a material that has a dielectric constant close to 1, which is the case for air:

$$Z = 60\ln\left(\frac{F_1 h}{w} + \sqrt{1 + \left(\frac{2h}{w}\right)^2}\right) \tag{11}$$

with $$F_1 = 6 + (2\pi - 6)\exp\left(-\left(30.666\,\frac{h}{w}\right)^{0.7528}\right). \tag{}$$

As seen in n Eq. (11), the sensor impedance is a function of the signal trace width, w, and the spacing between the signal and ground trace, h, that must be adjusted to obtain a desired impedance of 50Ω.

The role of the electrical trace is to convert the locations of the contact edges between the bilayer beam and the rigid base to phase values. Indeed, the phase shifts measured on both ends of the sensor are a function of the length traveled by the electromagnetic wave in the trace. Matching the sensor impedance as described in the previous section ensures that we obtain a linear relationship between the length traveled by the wave on the signal trace and the phase that it accumulates in the process. Generally, this linear relationship between phase and length travelled, l, is given by Eq. (12):

$$\Delta\phi = \gamma\Delta x, \text{ with } \gamma = \frac{2\pi f}{c} \tag{12}$$

where c is the speed of light, i.e., the speed of the electromagnetic wave in the signal trace, and f its frequency. When the force sensor is pressed, the separation between the signal trace and ground trace tapers down from height h to 0 at the contact point. For such tapered transmission lines, the propagation exponent has the form of $(1-e^{-\gamma\Delta x})$, which has a phase of $-\gamma/2\,\Delta x$, instead of $-\gamma\Delta x$ for parallel transmission lines. This leads to the new relationship $\Delta\phi = \gamma/2\,\Delta x$. Finally, the phase accumulated for a displacement of a contact edge between the traces of $\Delta x$ must be doubled, as the wave follows the path once, is reflected at the shorting location, and travels back along the same path. Simplifying the coefficients results in the relationship between the contact edge displacement and the measured phase, as given by Eq. (13):

$$\Delta\phi = \left(\frac{2\pi f}{c}\right)\Delta x \tag{13}$$

To ensure unicity of the phase measurement, the length of the signal trace must be limited to the wavelength of the signal that travels along it. Thus, the maximum signal trace length, which is also the maximum bilayer beam length, $L_{max}$, is given by Eq. (14). This relationship is a design rule that must hold for both the trace and the bilayer beam length.

$$L_{max} = \frac{1}{2}\left(\frac{c}{f}\right) \tag{14}$$

where "c" is the speed (of light) of the electromagnetic wave in the signal trace and "f" is the frequency of the electromagnetic wave.

Wireless Phase Measurement

The wireless reader 120 can include both a transmit antenna and a receive antenna. A single antenna can be used if the wireless reader is configured to perform channel estimation. The reader 120 transmits an excitation signal, s(t), which is received and reflected by the sensor. A summation of both the reflected signal, as well as the excitation signal, are then read at the receive antenna. The signal reflected by the sensor must first be distinguished from the excitation signal. To achieve this, the signal received by the sensor can be modulated with a low power On-Off Keying (OOK) modulation, before being reflected back. This approach consists of a multiplication of the reflected signal by a square wave of frequency $$f_s = \frac{1}{T_s},$$

where $T_s$ is its on-off time period. The reflected signal, r(t), after OOK modulation of s(t) is therefore given by r(t)=m(t)s(t), where m(t) is given by Eq. (15):

$$m(t) = \begin{cases} 0, nT_s \le t < \left(nT_s + \dfrac{T_s}{2}\right) \\ 1, \left(nT_s + \dfrac{T_s}{2}\right) \le t < (n+1)T_s, n \in \mathbb{Z} \end{cases} \tag{15}$$

Expanding m(t)'s Fourier series, the sum of the odd harmonics is obtained using Eq. (16).

$$m(t) = \sum_{k \in (2i+1), i \in \mathbb{Z}} \frac{1}{|k|} e^{(j2\pi k f_s t)} \tag{16}$$

Ignoring the weaker high order harmonics, the reflected r(t) is given by Eq. (17).

$$r(t) = s(t)m(t) \approx s(t)e^{j2\pi f_s t} \tag{17}$$

This approach leads to the reflected signal being shifted in the frequency domain by $f_s$, the frequency of the square wave, thus isolated the reflected signal from the emitted signal. In order to measure the phase changes on both ends of the signal trace independently, without interference from the opposite end, RF switches on both ends of the sensor are toggled at different frequencies $f_{s1}$, $f_{s2}$. The signals reflecting from the two ends of the sensor thus give the accumulated phases $\phi1$, $\phi2$, in addition to the modulations at frequencies $f_{s1}$ and $f_{s2}$.

Figure 6A:
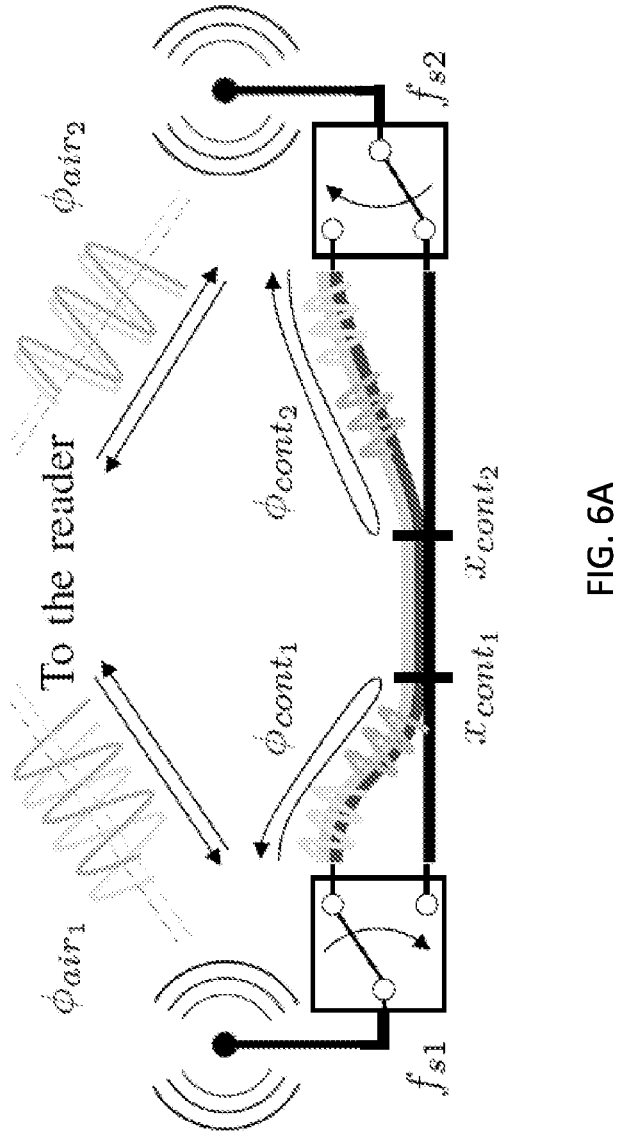
FIG. 6A illustrates how a force acts on a preferred sensor and the beam touches the rigid base between the contact locations $x_{cont1,2}$, and that the phases measured by the reader are a sum of two phases, $\phi_{air1,2}$ and $\phi_{cont1,2}$.

Once the signal reflected by the sensor can be measured by the reader, the next step is to extract the phases of the signals reflected at the shorting locations of the signal and ground trace of the sensor. When a force acts on the sensor and the bilayer beam touches the rigid base between the contact locations $x_{cont1,2}$, the phases measured by the reader are a sum of two phases, $\phi_{air1,2}$ and $\phi_{cont1,2}$, as illustrated in FIG. 6A. The phases $\phi_{air1,2}$ are due to the presence of air between the sensor and the reader. The phases of interest, $\phi_{cont1,2}$, are due to the signals that travel from end 1 and 2 of the sensor, respectively, until the contact edges, and reflect back from there. They are given by Eq. (18);

$$\phi_{cont1} = \left(\frac{2\pi f}{c}\right)x_{cont1}, \phi_{cont2} = \left(\frac{2\pi f}{c}\right)x_{cont2} \qquad (18)$$

This leads to total phases measured at both ends of the sensor given by Eq. (19).

$$\begin{cases} \phi_{force1} = \phi_{air1} + \phi_{cont1} \\ \phi_{force2} = \phi_{air2} + \phi_{cont2} \end{cases} \qquad (19)$$

Figure 6B:
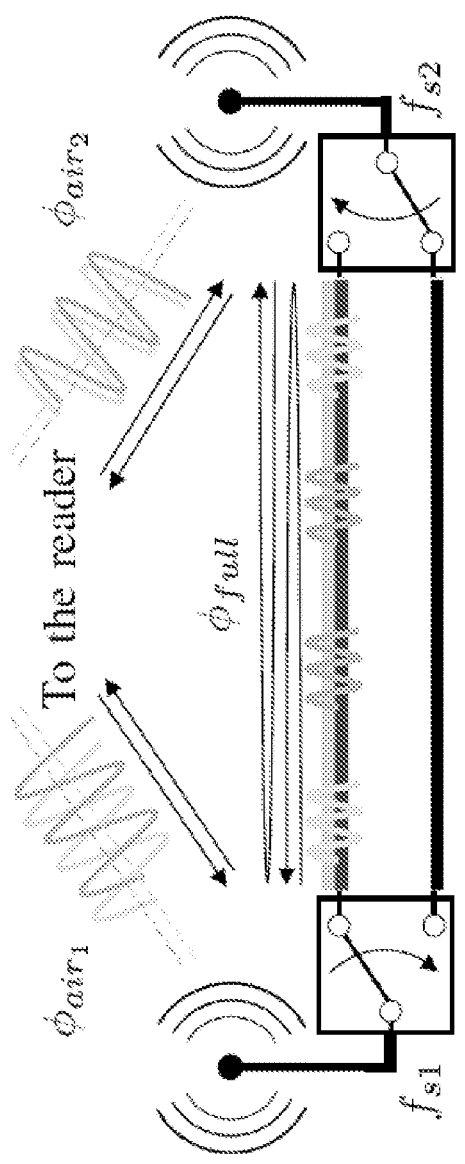
FIG. 6B is labelled with phases as in FIG. 6A for a measurement when the sensor is not subjected to a force.

As visible in Eq. (19), the phases of interest $\phi_{cont1,2}$ cannot be measured directly, as they are added to the phases due to the presence of air between the sensor and the reader. In order to cancel these added phases, a differential measurement is performed between the sensor pressed and the sensor at rest. Indeed, when no force is applied on the sensor, phases $\phi_{noforce1,2}$ are measured at both ends, as illustrated in FIG. 6B. These phases are given by Eq. (20).

$$\begin{cases} \phi_{noforce1} = \phi_{air1} + \phi_{full} \\ \phi_{noforce2} = \phi_{air2} + \phi_{full} \end{cases} \qquad (20)$$

with $\phi_{full}$ a constant given by Eq. (21).

$$\phi_{full} = \left(\frac{2\pi f}{c}\right)L \qquad (21)$$

By measuring the phase changes (i.e. the difference between the phase measured by the reader before and after a force is applied), the phases due to the presence of air between the sensor and the reader are canceled, as shown in Eq. (22).

$$\begin{cases} \phi_{noforce1} - \phi_{force1} = \phi_{full} - \phi_{cont1} = \phi_1 \\ \phi_{noforce2} - \phi_{force2} = \phi_{full} - \phi_{cont2} = \phi_1 \end{cases} \qquad (22)$$

Hence, the additional phase due to the presence of air can be removed, and the desired phase information can be obtained, enabling the measurement of the phases due to the displacement of the shorting points on the signal trace.

Prototype Design and Fabrication

To start a design, a first step is to select frequency for the sensor. As shown in Eq. (13), the frequency of the sensor can be maximized to accumulate the maximum phase change on both ends of the sensor, and thus increase the resolution. For medical applications, signal losses increase as a wave goes trough human tissue for frequencies higher than 1 GHz. To test such an application, a frequency (f) equal to 915 MHz was selected for the prototype. The choice of frequency allows computation of the maximum signal trace and bilayer beam lengths to avoid phase redundancy measurements, as given by Eq. (14). For a frequency of f=915 MHz and a celerity of wave in the electrical trace, c, approximated by the speed of light in the void (299×106 m/s), we obtain a maximum length of $L_{max}$=164 mm, that must hold for the sensor.

The next step in the design process is the mechanical implementation. A prototype design goal was to sense forces between 2 and 8 N, on 50% of its length. Because the sensor is less sensitive close to its edges, we center this area in the middle of the sensor, at x=L/2. As the maximum deflection of the sensor is an increasing function of $F_{loc}$ (for $F_{loc} \leq L/2$), the critical location to ensure a minimum force detection of 2 N is at $F_{loc}$=L/4. By replacing $F_{mag}$ with 2 N and $F_{loc}$ with L/4 in Eq. (9), the design rule that must be respected for our prototype is then given by Eq. (23):

$$h = \frac{27L^3(E_1\delta_1 + E_2\delta_2)}{400W\left(E_1^2\delta_1^4 + 4E_1E_2\delta_1^3\delta_2 + 6E_1E_2\delta_1^2\delta_2^2 + 4E_1E_2\delta_1\delta_2^3 + E_2^2\delta_2^4\right)} \qquad (23)$$

The prototype mechanical components' characteristics are in the following table:

| Parameter | Bottom layer (#1) | Top layer (#2) |
|---|---|---|
| Material | Ecoflex 00-30 | Acrylic |
| Young modulus E (Pa) | $125 \times 10^3$ | $2 \times 10^9$ |
| Poisson's Ratio | 0.49 | 0.35 |
| Thickness $\delta$ (mm) | 2.54 | 1.4 |
| Width W (mm) | 9.85 | |
| Length L (mm) | 80 | |
| Spacer height h (mm) | 0.64 | |
| Trace width w (mm) | 2.5 | |

These parameters allow Euler-Bernoulli's hypothesis to be respected, with a bilayer beam solely made out of the material of layer 1 (leading to 0.00074<<1) and a bilayer beam solely mode out of the material of layer 2 (leading to 0.00067<<1) (see Eq. (6)). They also verify Eq. (23), and we have L. $L_{max}$. For force application locations of 20, 30, 40, 50 and 60 mm along the sensor, the forces for initial contact are 2.00, 1.25, 1.08, 1.25 and 2.00 N, respectively, which satisfy the requirements in terms of minimum force to be sensed, and the contact locations are 32, 35.6, 40, 44.4 and 48 mm, respectively.

FEA was used to quantify the locations of the contact edges between the beams as a force is applied to it, to ensure that a significant phase change can be obtained. For this purpose, we used COMSOL Multiphysics (COMSOL, Inc., Burlington, USA) to model the sensor beams and perform the analysis. The bottom layer of the bilayer beam, made out of Ecoflex 00-30, is modeled using the hyperelastic Yeoh model, with $C_1$=17 KPa, $C_2$=−0.2 KPa and $C_3$=0.023 kPa. The initial bulk modulus is computed using the relationship $$k = \frac{E}{3(1-2v)},$$

with a Poisson's ratio of 0.49. The location of the applied forces are 20, 30, 40, 50 and 60 mm, and the force magnitude for each location is varied between 0 and 8 N in 0.1 N increments. The resulting bilayer beam shapes for initial contact or 4 N, and 8 N of applied force was considered, and the contact length increases when the force applied on the beam increases, and goes from a single initial contact point to a contact length (computed as $x_{cont2}-x_{cont1}$) of 28.7 mm on average for all force locations assessed, for a force of 8 N. Using Eq. (13), this variation of overall contact length of 28.7 mm corresponds to an accumulated phase change of 31.5 degrees, which means approximately 4 degrees/N, which is a satisfactory resolution, thus validating the mechanical design.

The last implementation step is the design of the electrical trace. Using Eq. (11) with a desired impedance of Z=50Ω and a spacer height of h=0.64 mm, the trace width is computed to be 4.75 mm. However, because the dielectric between the signal and ground trace is not only made of air, since plastic spacers separate the traces at both ends of the sensor, we found that a lower value of 2.5 mm works better in practice. This is thus the adopted value in our design.

Figure 7A:
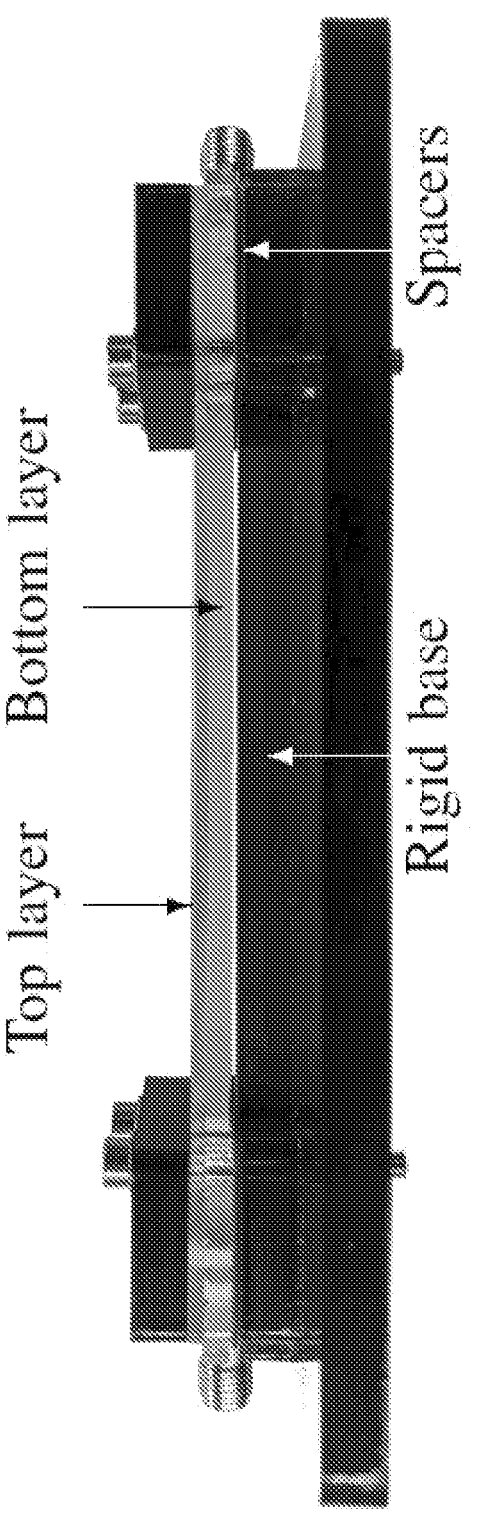
FIGS. 7A and 7B are respective side and top view images of an example prototype sensor of the invention.
Figure 7B:
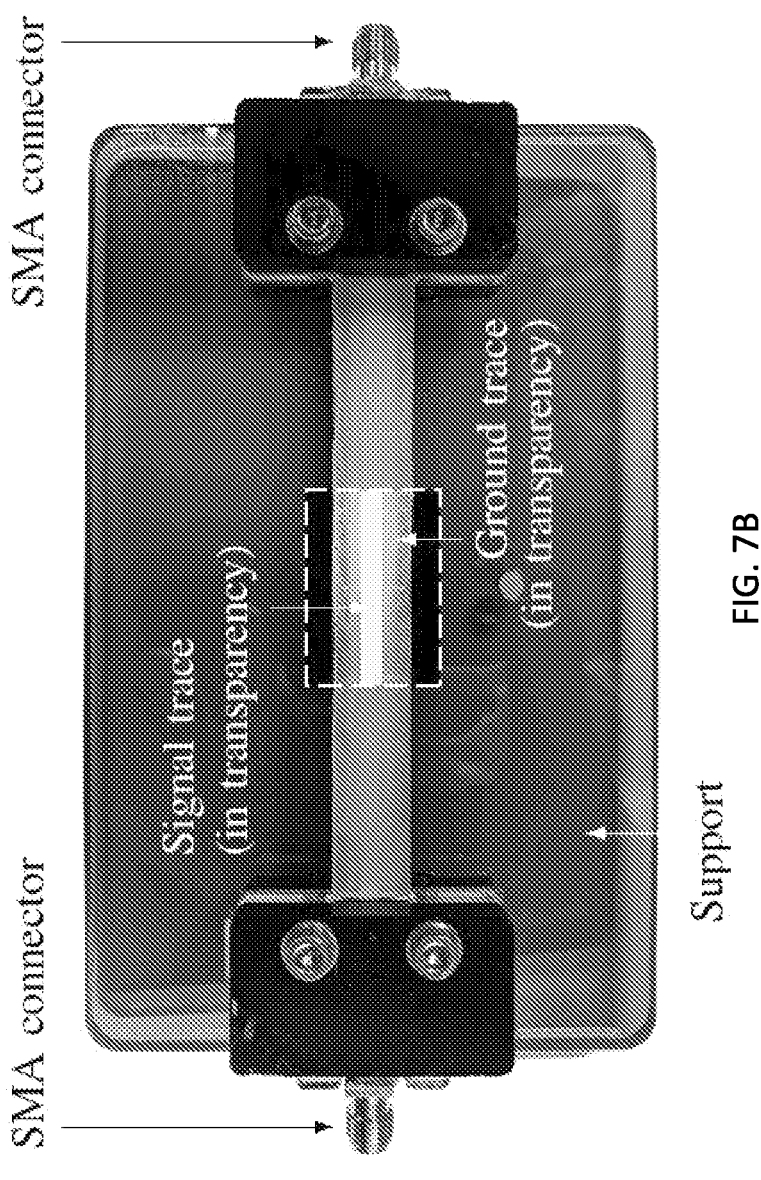

FIGS. 7A (side view) and 7B (top view) how the fabricated sensor. The top layer was laser-cut from an acrylic sheet with the desired thickness. The bottom layer was created by molding Ecoflex 00-30 between two acrylic sheets spaced by 2.54 mm. These two fabricated layers were then glued together with cyanoacrylate, and are visible in FIG. 7A. The signal trace was fabricated by applying a thickness of 0.06 mm of Fast Drying Silver Paint (Ted Pella, Inc., CA, USA) onto a 0.1 mm thick plastic film that was glued onto the bottom side of the Ecoflex 00-30 layer with cyanoacrylate. The ground trace was fabricated using copper tape with a width of 6.4 mm and a thickness of 0.06 mm, applied directly onto the rigid base, and SMA connectors were soldered on both ends of the traces, as visible in FIG. 7B, to allow an electrical access to them by the switches and the antenna.

Testing of the sensor showed that measurements are repeatable, and close to the expected, ideal behavior. The average error and standard deviation between the sensor's readings load cell readings were 0.01 N and 0.49 N, respectively, while the average error and standard deviation between the sensor readings and the force application locations were −0.33 mm and 0.82 mm, respectively.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A wireless force sensor, comprising:
a flexible structure supported opposing a rigid structure with a gap between the flexible structure and the rigid structure;
contact traces on opposing surfaces of the flexible structure and the rigid structure, the contact traces forming transmission lines, the contract traces being aligned to contact when a force is applied the flexible structure to cause contact between the traces on the opposing surfaces;
radio-frequency switches to modulate a reflected signal from the transmission lines; and
an antenna to receive an interrogation signal and to transmit the reflected signal.

2. The wireless force sensor of claim 1, wherein the flexible structure comprises a bilayer with having a stiffer layer and a softer layer, wherein the softer layer is closer to the rigid structure.

3. The wireless force sensor of claim 2, wherein softer layer comprises a soft polymer.

4. The wireless force sensor of claim 3, wherein the soft polymer is a soft silicon rubber.

5. The wireless force sensor of claim 4, wherein the stiffer layers is a thermoplastic material.

6. The wireless force sensor of claim 1, wherein the flexible structure is configured to provide different contact patterns of the transmission lines in response to different applied forces.

7. The wireless force sensor of claim 1, wherein the contact traces comprise straight transmission lines.

8. The wireless force sensor of claim 1, wherein the contact traces comprise meandering transmission lines.

9. The wireless force sensor of claim 1, wherein the transmission lines have a length that is less than a wavelength of the interrogation signal.

10. The wireless force sensor of claim 1, wherein the flexible structure comprises a suspended beam, the contract traces comprise microstrip lines.

11. The wireless force sensor of claim 1, wherein the contact traces on the flexible structure is a signal line connected to the RF switches and the contract trace on the rigid structure is a ground line.

12. The wireless force sensor of claim 1, comprising clock source, wherein the RF switches are configured to communicate backscattered phases to a wireless reader.

13. A system including the wireless force sensor of claim 1, and a wireless reader, the reader comprising hardware to emit an excitation signal and receive a reflected signal and correlate the reflected signal to an amount and location of force on the flexible structure reflected signal via low power On-Off Keying.

14. The wireless force sensor of claim 1, wherein the RF switches are configured to emit the reflected signal at a unique phase from the interrogation signal.

15. The wireless force sensor of claim 1, formed as a tag applied to an object.

* * * * *